(12) United States Patent
Widmer et al.

(10) Patent No.: US 7,879,379 B1
(45) Date of Patent: Feb. 1, 2011

(54) METHOD OF PRETREATING CITRUS WASTE

(75) Inventors: Wilbur Widmer, Winter Haven, FL (US); David Stewart, Boca Raton, FL (US); Karel Grohmann, Davenport, FL (US); Mark Wilkins, Stillwater, OK (US)

(73) Assignees: The United States of America as represented by the Secretary of Agriculture, Washington, DC (US); Renewable Spirits LLC, Boca Raton, FL (US)

( * ) Notice: Subject to any disclaimer, the term of this patent is extended or adjusted under 35 U.S.C. 154(b) by 1107 days.

(21) Appl. No.: 11/603,277

(22) Filed: Nov. 21, 2006
(Under 37 CFR 1.47)

(51) Int. Cl.
*C07C 31/08* (2006.01)
(52) U.S. Cl. .................. 426/481; 426/492; 426/494; 426/599
(58) Field of Classification Search ............... 426/481, 426/492, 494, 599; 435/283.1–309.4
See application file for complete search history.

(56) References Cited

U.S. PATENT DOCUMENTS

| | | | |
|---|---|---|---|
| 1,973,084 A | 9/1934 | Lewis | |
| 2,276,420 A | 3/1942 | Rosenfeld et al. | |
| 2,471,893 A | 5/1949 | Pulley | |
| 2,625,488 A | 1/1953 | Wasserman et al. | |
| 2,774,671 A * | 12/1956 | Cotton et al. ............... | 426/635 |
| 3,745,020 A | 7/1973 | Lime et al. | |
| 3,862,014 A | 1/1975 | Atkins et al. | |
| 3,966,984 A | 6/1976 | Cocke et al. | |
| 4,113,573 A | 9/1978 | Gerow | |
| 4,291,124 A | 9/1981 | Muller et al. | |
| 4,313,372 A | 2/1982 | Gerow et al. | |
| 4,326,926 A | 4/1982 | Gerow | |
| 4,334,962 A | 6/1982 | Gerow | |
| 4,488,912 A | 12/1984 | Milch et al. | |
| 4,490,469 A | 12/1984 | Kirby et al. | |
| 4,497,838 A | 2/1985 | Bonnell | |
| 4,503,079 A | 3/1985 | King et al. | |
| 4,547,226 A | 10/1985 | Milch et al. | |
| 4,564,595 A | 1/1986 | Neves | |

(Continued)

OTHER PUBLICATIONS

Jacques, K., et al., "Ethanol Distillation: The Fundamentals", *The Alcohol Textbook*, 2003, pp. 325-326.

(Continued)

*Primary Examiner*—Anthony Weier
(74) *Attorney, Agent, or Firm*—John D. Fado; G. Byron Stover

(57) ABSTRACT

Method of pretreating citrus waste to break cell structure, pasteurize or sterilize citrus waste solids and remove inhibitory peel oil components (e.g., limonene) involving optionally reducing the particle size of the citrus waste prior to preheating, preheating the citrus waste through indirect heating in a preheater reactor to form preheated citrus waste and conveying the preheated citrus waste to a main reactor, heating the citrus waste through a combination of (simultaneous) indirect heating and direct heating to produce treated citrus waste solids that are pasteurized and a vapor containing water and peel oil components, separating the pasteurized citrus waste solids and the vapor containing water and peel oil components, and collecting the separated vapor containing water and peel oil components by condensation. The method optionally includes cooling the pasteurized citrus waste solids followed by saccharifying with enzymes and fermentation to produce ethanol or other products.

14 Claims, 2 Drawing Sheets

U.S. PATENT DOCUMENTS

| | | | |
|---|---|---|---|
| 4,637,835 A | 1/1987 | Nagle | |
| 4,650,689 A | 3/1987 | Hedrick | |
| 4,818,250 A | 4/1989 | Whitworth | |
| 4,915,707 A | 4/1990 | Whitworth | |
| 4,938,985 A | 7/1990 | Swaine, Jr. et al. | |
| 4,952,504 A | 8/1990 | Pavilon | |
| 4,971,813 A | 11/1990 | Strobel et al. | |
| 4,973,485 A | 11/1990 | Rich | |
| 5,100,679 A | 3/1992 | Delrue | |
| 5,135,861 A | 8/1992 | Pavilon | |
| 5,198,074 A | 3/1993 | Villavicencio et al. | |
| 5,259,945 A | 11/1993 | Johnson, Jr. et al. | |
| 5,470,478 A | 11/1995 | Leva | |
| 5,571,703 A | 11/1996 | Chieffalo et al. | |
| 5,915,815 A | 6/1999 | Moore et al. | |
| 6,076,362 A | 6/2000 | Hubinger et al. | |
| 6,143,337 A | 11/2000 | Fishman et al. | |
| 6,151,799 A | 11/2000 | Jones | |
| 6,183,806 B1 | 2/2001 | Ficca et al. | |
| 6,251,643 B1 | 6/2001 | Hansen et al. | |
| 6,267,309 B1 | 7/2001 | Chieffalo et al. | |
| 6,753,028 B2 | 6/2004 | Iada et al. | |
| 6,766,595 B2 | 7/2004 | Anderson | |
| 6,962,722 B2 | 11/2005 | Dawley et al. | |
| 7,060,313 B2 | 6/2006 | Jones | |
| 2002/0031581 A1 | 3/2002 | Baker, IV | |
| 2004/0063184 A1 | 4/2004 | Grichko | |
| 2004/0091983 A1 | 5/2004 | Veit et al. | |
| 2004/0170731 A1 | 9/2004 | Subramaniam et al. | |
| 2004/0253696 A1 | 12/2004 | Grichko | |
| 2005/0054064 A1 | 3/2005 | Talluri et al. | |
| 2006/0154352 A1 | 7/2006 | Foody et al. | |
| 2007/0082385 A1 | 4/2007 | Smith et al. | |
| 2007/0190620 A1 | 8/2007 | Mueller | |
| 2008/0227166 A1 | 9/2008 | Allain et al. | |

OTHER PUBLICATIONS

McDonald, K., et al., "Vacuum Cooling Technology for the Food Processing Industry: A Review", *J. of Food Engineering*, vol. 45, 2000, pp. 55-65.

www.floridachemical.com/whatisd-limonene.htm.

Grohmann, K., et al., "Production of Ethanol from Enzymatically Hydrolized Orange Peel by the Yeast Saccharomyces cervisiae", Applied Biochemistry and biotechnology, vol. 45/46, pp. 315-327, 1994.

Grohmann, K., et al., "Fermentation of Sugars in Orange Peel Hydrolysates to Ethanol by recombinant *Escherichia coli* KO11", Applied Biochemistry and biotechnology, vol. 51/52, pp. 423-435, 1995.

Gerow, G., "Economics of d-limonene recovery", Transcript of the 1974 citrus Engineering conf., ASME, vol. 20, 1974, pp. 61-66.

Kesterson, J.W., et al., "By-Products and Specialty Products of Florida Citrus", Institute of food and Agricultural Sciences, Dec. 1976, 2003, pp. 8, 102, and many others.

Pan, X., et al., "Strategies to Enhance the Enzymatic Hydrolysis of Pretreated softwood with High Residual Lignin Content", Applied Biochemistry and biotechnology, vol. 121-124, 2005.

Kelsall, D., et al., "Grain dry milling and cooking procedures: extracting sugars in preparation for fermentation". The Alcohol Textbook, 2003, pp. 17-19.

Kling, S., et al., "Enhancement of Enzymatic Hyrolysis of Sugar Cane Bagasse by steam Explosion Pretreatment", Biotechnology and Bioengineering. vol. 19, 1987, pp. 1035-1039.

Philippidis, G., et al., "Study of the Enzymatic Hydrolysis of cellulose for Production of Fuel Ethanol by the Simultaneous Saccharification and fermentation Process", Biotechnology and Bioengineering, vol. 41, 1993, pp. 846-853.

Lane, A.G., 1980, Journal Chem. Tech. Biotechnol., 30. pp. 345-350.

Mizuki, E., Akao, T., and Saruwatari, T., 1990, Biol Wastes, 33. pp. 161-168.

\* cited by examiner

METHOD OF PRETREATING CITRUS WASTE

BACKGROUND OF THE INVENTION

This invention relates generally to citrus waste processing, and more particularly to pretreatment of citrus waste, primarily peel, to remove antimicrobial substances, to pasteurize or sterilize such waste and aid subsequent saccharification and fermentation to ethanol or other products. More specifically, the present invention relates to a method of pretreating citrus waste to remove peel oil components (e.g., limonene) involving preheating the citrus waste through indirect heating in a preheater reactor to form preheated citrus waste and conveying the preheated citrus waste to a main reactor, heating the preheated citrus waste through a combination of (simultaneous) indirect heating and direct heating in a main reactor to produce pasteurized citrus waste solids and a vapor containing water and peel oil components, and separating the pasteurized citrus waste solids and the vapor containing water and peel oil components to produce separated pasteurized citrus waste solids low in peel oil content and with disrupted cell structure and a separated vapor containing water and peel oil components. The method optionally further involves cooling the separated pasteurized citrus waste solids and saccharifying and fermenting the cooled pasteurized citrus waste solids using enzymes and yeasts or other microorganisms. The method optionally further involves reducing the particle size of the citrus waste prior to preheating.

Additionally, the present invention relates to a system for pretreating citrus waste to remove peel oil components from the citrus waste involving conveying means to convey citrus waste into and through the system; indirect preheating means to preheat the citrus waste; indirect and direct heating means to heat the preheated citrus waste and produce pasteurized citrus waste solids and a vapor containing water and peel oil components; separating means to separate the pasteurized citrus waste and vapor containing water and peel oil components to produce separated pasteurized citrus waste solids and separated vapor containing water and peel oil components; heat recovery means to convey separated vapor containing water and peel oil components to the indirect preheating means; and optionally size reducing means to reduce the particle size of the citrus waste prior to preheating. The system optionally includes cooling means for cooling the separated pasteurized citrus waste solids and means for saccharifying and fermenting such cooled waste.

Development of industrial plants for processing of citrus crops to juice products created environmental problems involving disposal of peel, seeds and membranes (rags) which collectively comprise citrus waste. The major problem exists in areas with large scale processing of orange and grapefruit crops to juice, such as the State of Florida or country of Brazil. Approximately 3 to 5 million tons of citrus processing waste is produced annually in the State of Florida alone. While a small portion of the processing waste is delivered directly to cattle pastures, the majority is pressed and dried to cattle feed. The large equipment and energy costs for dewatering, drying and transportation of citrus waste are usually not recovered due to the low value of citrus waste as cattle feed.

In addition citrus waste contains significant amounts (e.g., 0.3 to 1.7%) of essential (peel) oil, composed mainly (e.g., 90-99 wt %) of d(+)-limonene. Oil vapors escape to exhaust gases during drying and have to be removed by expensive scrubbing systems or cause air pollution. Although citrus processing waste creates problems for industry, it is rich in soluble sugars and polymeric carbohydrates such as pectin, cellulose and hemicelluloses. These polymeric carbohydrates can be hydrolyzed to simple sugars by the action of acids or preferably enzymes known in the art, and these additional sugars can be fermented to ethanol, lactic acid or other products by methods known in the art. Citrus processing waste has unique aspects which differentiate it from many other plant (i.e., lignocellulosic) feedstocks. It does not contain significant amounts of lignin, instead it contains a pectin-hemicellulose matrix. The major hemicelluloses in citrus waste are arabinans and galactans, whereas in lignocellulosic materials they are xylans or glucomannans. The lack of lignin makes citrus waste easier to hydrolyze by enzymes although a complex of pectinases, cellulases and hemicellulases is needed for efficient hydrolysis. Pectin and cellulose are also highly resistant to acid hydrolysis. Another unique characteristic of citrus processing waste is its high content of soluble sugars which are held in spongy tissues as a liquid solution (juice). These sugars require only collapse or disrupture of plant tissue to be efficiently released by pressing, diffusion or similar processes.

Citrus waste also contains potent antimicrobial components in peel oil. Oil is present in specialized cells (glands) of the outer part of the peel (flavedo). In order to achieve efficient fermentation to ethanol, limonene and possibly other volatile components of peel oil have to be reduced to a level below about 3,000 parts per million (ppm) (e.g., <3000 ppm; preferably to less than about 1500 ppm (e.g., <1500 ppm)); the exact inhibitory concentrations of limonene depend on the tolerance of individual microorganisms employed in the fermentation process. It is also desirable to recover limonene and preferably peel oil because they are valuable industrial chemicals and flavoring agents.

Treatments of citrus waste prior to saccharification need to retain relatively high sugar concentrations present in this waste since higher concentrations of ethanol and other fermentation products then accumulate with attendant savings in fermentation and recovery costs. Therefore the addition of water or other diluents during the process need to be reduced to a minimum.

Since peel oil is concentrated in specialized cells, these cells need to be pierced or ruptured by mechanical or other means to free the oil from citrus waste tissue. This is currently accomplished by piercing or squashing the peel of citrus fruit before or during extraction of juice. The surface of the fruit is washed with a stream of water and the resulting emulsion is separated by decanting and preferably by centrifugation. These methods remove approximately 50% of the oil from peel, but the residual concentration (3,500-15,000 ppm) is still too high to allow fermentation of citrus waste to ethanol or other products.

One of the current methods which can be applied to removal of residual peel oil involves additional disintegration of citrus waste to fine particles and separation of the oil rich fraction by flotation or centrifugation. Other methods include solvent, detergent or other chemical extraction of citrus waste slurries. All these methods suffer from extensive dilution of waste and sugars with water, detergent solutions or organic solvents. The organic solvents and detergents are often toxic or deleterious to fermentation microorganisms and the environment.

While citrus waste at 70-85% moisture contains sufficient amounts of water to strip volatile oil components when this moisture is converted to steam by indirect heating (U.S. Pat. No. 3,966,984), the indirect heating of undiluted citrus waste is a very inefficient process. Irregular solid pieces of peel and other particles of citrus waste do not have good contact with the surfaces of indirect heat exchangers and the slimy nature of some citrus waste components leads to fouling of heat exchanger surfaces resulting in further decreases in heat transfer rate and efficiency.

Efforts to improve poor contact with heat exchanger surfaces have involved blending waste with nontoxic heat transfer liquids such as water or by decreasing the particle size by shredding, milling or other particle size reduction methods. However, dilution of citrus waste with water is not an acceptable solution because it excessively dilutes the sugars for subsequent saccharification and fermentation. The comminution of peel to small particles does not satisfactorily solve the heat transfer problem because a very viscous paste is formed by this method. This viscous paste does not mix well and does not efficiently transfer heat from the surface of the heat exchanger to the bulk of citrus waste.

The need thus exists for development of new processes for a pasteurization treatment of citrus wastes at high concentration of solids and preferably under conditions mild enough to allow removal and recovery of peel oil with minimal degradation of limonene and other components and to facilitate and allow efficient enzymatic saccharification and fermentation of citrus waste.

We have determined that a combination of indirect and direct heat exchange is more efficient in heating citrus waste particles to temperatures necessary to rupture plant tissues and release volatile oil components. The indirect heat exchanging surface increases heat input to the process without diluting the citrus waste by steam condensate, and hot gas or vapors can enter between citrus waste particles and efficiently increase their temperature (direct heat exchange).

We have also determined that one of the devices suitable for our process is a jacketed and heated screw conveyor equipped with concurrent or countercurrent steam or hot gas injection. However other heated high solids mixers/conveyors such as pug mills, helical ribbon mixers or similar devices can also be used.

SUMMARY OF THE INVENTION

One object of the present invention is to provide a system and a method for pasteurization of citrus waste and which efficiently disrupts cell structure of the processing waste, and removes volatile peel oil components from citrus processing waste.

Another object of the present invention is to increase the recovery of peel oil, including limonene, to reduce air pollution from current citrus processing plants.

A further object of the present invention is to increase the recovery of peel oil, including limonene, from citrus waste in order to be sold as valuable byproduct.

Yet a further object of the present invention is to provide a pasteurization and cell disrupting pretreatment and peel oil removal method and system to provide suitable feedstock for subsequent saccharification and fermentation of citrus waste to ethanol and other products.

The present invention fulfills the above and other objects by providing a system and method for producing ethanol or other products from citrus waste that reduces microbial contamination and peel oil components that inhibit fermentation to such levels that fermentation to yield ethanol or other products can take place. The present invention also provides a method and system to remove and recover peel oil components, including limonene, with minimal degradation so they can be sold as high value byproducts.

This system includes optional means for reducing citrus waste particles to predetermined size when necessary for processing, utilizing for example a hammer mill, disc mill, grinder or similar shredding/chopping/grinding apparatus.

The citrus waste is then preheated to about 55°-about 99° C. (e.g., 55°-99° C.) using a jacketed, enclosed delayed conveyor (preheater reactor), e.g., screw, paddle or ribbon, to assure efficient contact between the citrus waste and the heating surfaces without undue compaction of the citrus waste. Jacketed screw conveyors can have a hollow shaft and hollow flights to provide additional heating surfaces. In a preferred embodiment of this invention, vapors from peel oil stripping (discussed below) are introduced to the heating jacket, hollow flights and other heating surfaces to condense the peel oil and water mixture and provide heat to the citrus waste in the preheater reactor; an optional condenser may be used to condense the peel oil and water mixture. Additional heat if required can be provided by concurrent, countercurrent or crossflow stream of hot gases, such as air, flue gases or superheated steam.

The particles of preheated citrus waste are then transferred to another conveyor (main reactor) where they are heated at elevated temperature to soften, disrupt, and break down the waste tissue material. The preheated citrus waste is fed into the main reactor, for example by a high solids pump, screw feeder or similar device. Preferred reaction time in the main reactor is about 1 to about 300 minutes (e.g., 1 to 300 minutes). Heating is conducted at sufficiently high temperature to soften, pre-treat and pasteurize the waste. The temperature must also be high enough to induce formation of a vapor component containing water and peel oil components when the material is released into a flash tank under a reduced pressure from that in the main reactor. However, the temperature in the main reactor must also be low enough to minimize degradation of peel oil components by thermal reactions. The heating temperature is generally between about 90° and about 200° (e.g. 90° to 200° C.), and most preferably between about 100° to about 160° C. (e.g., 100° to 160° C.). The pressure is generally from about barometric (atmospheric) to about 20 bar (300 psi) (e.g., barometric pressure to 20 bar). The heating operation is conducted in a jacketed, enclosed and pressurized delayed (e.g., screw, paddle or ribbon) conveyor/main reactor. The main reactor is provided with jacket and other heating surfaces for indirect heat transfer and injection ports for concurrent, crossflow or preferably countercurrent contact with heated gaseous medium (e.g., saturated steam, air, flue gas or superheated steam) to provide additional heat and stripping action for peel oil; superheated steam is a preferred medium for direct heat transfer in the device. Part of the peel oil/water vapor mixture can be bled from the main reactor (e.g., to indirectly preheat the preheater reactor/conveyor discussed above), condensed and separated into peel oil and water fractions by decantation, centrifugation or similar well known techniques. Additional and major portion of peel oil/water vapor fraction is obtained upon transfer of the reactor contents to atmospheric or optionally reduced pressure, which is accomplished by rotary or other similar valve or device at the exit from the main reactor, and separation of solid and vapor fractions in a cyclone or similar flash tank device. The peel oil/water vapor mixture is used to indirectly preheat the conveyor (preheater reactor) discussed above, where the vapor is condensed and separated into peel oil and water fractions by decantation, centrifugation or similar well known techniques.

After the peel oil, including limonene, has been reduced to a sufficiently low level (e.g., below about 3,000 parts per million (ppm) (e.g., <3000 ppm) or preferably to less than about 1500 ppm (e.g., <1500 ppm)), citrus waste is optionally cooled (e.g., by vacuum, direct, or indirect heat exchange means), hydrolyzed to liquefy and release additional sugars by adding a mixture of cellulolytic, hemicellulolytic and pectinolytic enzymes, and then fermented to ethanol or other products by yeast or other suitable microorganisms. The pH of the citrus waste is controlled throughout the process in the range of pH about 1 to about 13 (e.g., pH 1-13) by addition of acids and bases to separately optimize the pretreatment, enzymatic hydrolysis and fermentation by microorganisms. The pretreated citrus waste may be subjected to additional particle size reduction if needed in subsequent processing steps.

The above and other objects, features and advantages of the present invention should become even more readily apparent to those skilled in the art upon reading of the following detailed description in conjunction with the drawings wherein there is shown and described illustrative embodiments of the invention.

DESCRIPTION OF THE PREFERRED EMBODIMENTS

Figure 1:
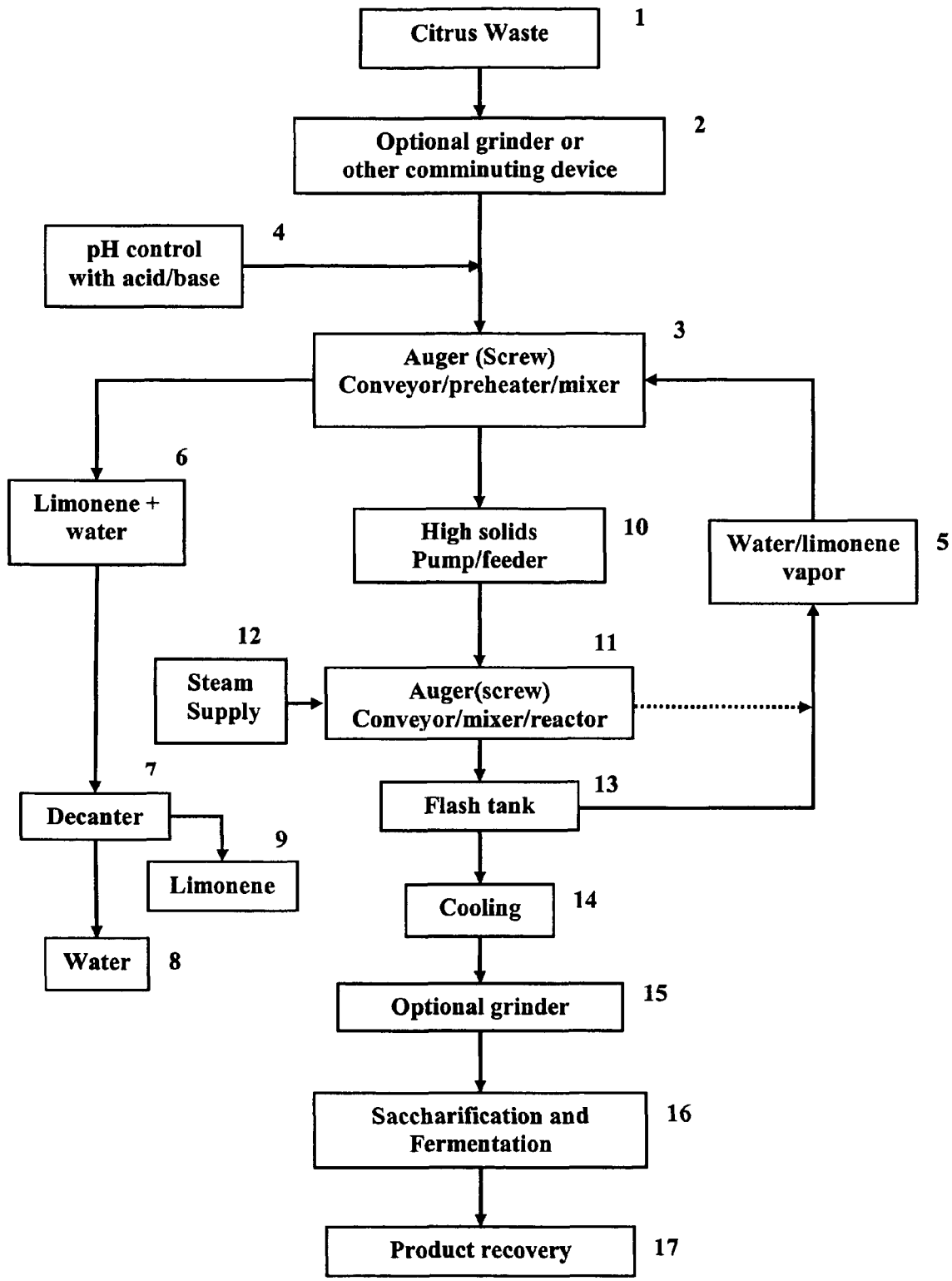
FIG. 1 shows a block diagram illustrating the pretreatment, saccharification and fermentation process of the present invention in which peel oil, including limonene, is removed by heating using an auger(screw) main reactor and the citrus waste cell solids are disrupted and pasteurized to facilitate subsequent saccharification and fermentation. Both peel oil and heat in peel oil/water vapors are recovered in a pre-heater device.

For purposes of describing the preferred embodiment, the terminology used in reference to the numbered components in the drawings is as follows:
1. Citrus waste mixture
2. Optional grinder, shredder or similar device
3. Jacketed auger conveyor/pre-heater/mixer/reactor
4. pH control with acid or base
5. Water/peel oil vapors, including limonene
6. Water/peel oil condensate, including limonene
7. Decanter
8. Water (bottom) layer
9. Peel oil layer, including limonene
10. High solids pump, auger or similar pressure feeder
11. Jacketed, auger conveyor/mixer/main reactor equipped with steam injection
12. Steam supply
13. Flash tank
14. Cooling system
15. Optional grinder, shredder or similar device
16. Saccharification and fermentation system
17. Product recovery system
18. Belt conveyor
19. Jacketed, auger conveyor/mixer with hollow shaft and hollow flights
20. Screw feeder, progressing cavity or similar pumping device
21. Rotary or check valve
22. Jacketed, enclosed delayed conveyor/mixer/reactor
23. Pressure relief valve
24. Rotary, backpressure regulated or similar discharge valve
25. Flash tank
26. Discharge auger or pump device
27. Steam/peel oil vapor return
28. Optional condenser
29. peel oil/water condensate Referring to FIG. 1, there is depicted a block diagram of a typical process according to this invention. Citrus waste 1, consisting primarily of peel, can be optionally reduced to size suitable for further processing by hammer mill, disc mill or other suitable grinders, choppers, shredders and mills 2. The waste is fed into an enclosed, jacketed agitating screw, ribbon or cut flight conveyor (preheater reactor) 3 which may have hollow shaft and flights. The waste is preheated by water/limonene (peel oil) vapor 5 (discussed below) condensing in the jacket and hollow flights of conveyor 3. The citrus waste pH may be adjusted by adding acid or base 4 to the agitating conveyor 3. The condensed peel oil/water emulsion 6 from conveyor 3 is fed into a decanter 7 or a centrifuge, where peel oil 9 is separated as a top layer and collected from the bottom water layer 8. The preheated citrus waste from conveyor 3 is fed into a main reactor 11 consisting of an enclosed and jacketed agitating screw, ribbon or cut flight conveyor/mixer where the main heating, pasteurization, and cell disruption reactions are conducted. The waste is fed into main reactor 11 using progressing cavity pump, screw feeder or similar pumping device 10 for compressible solids. The agitating conveyor/reactor 11 is equipped with injectors for steam 12 or other hot vapors or gases for direct heating and may have a hollow shaft and flights for indirect heating. The citrus waste pH may be in the range of pH about 1 to about 13 (e.g., pH 1-13; preferred pH about 2 to about 11 (e.g., pH 2-11)) and it is heated to temperatures between about 90° and about 200° C. (e.g., 90° to 200° C.; preferably between about 100° and about 160° C. (e.g., 100° to 160° C.)) for about 1 to about 300 minutes (e.g., 1-300 minutes) at about 0 to about 300 psi. (e.g., 0-300 psi). The heating is accomplished by a combination of indirect heating through jacket, hollow flights or similar heat exchanging surfaces and direct injection of steam or other hot vapors or gases into the main reactor 11 with the citrus waste being heated and pasteurized. Part of the vapors may be bled into the peel oil/water vapor line 5 to heat conveyor 3 (discussed above). The reacted, hot citrus waste is released into a flash tank 13 where peel oil/water vapors are separated from pretreated citrus waste solids through peel oil/water vapor line 5 to heat conveyor 3 (discussed above). The de-oiled and pasteurized citrus waste solids are then cooled by vacuum, direct or indirect heat exchange means 14, optionally ground to fine particles in shredding, chopping or grinding apparatus 15, and fed to saccharification and fermentation system 16 which is coupled to product (e.g., ethanol) recovery 17.

Figure 2:
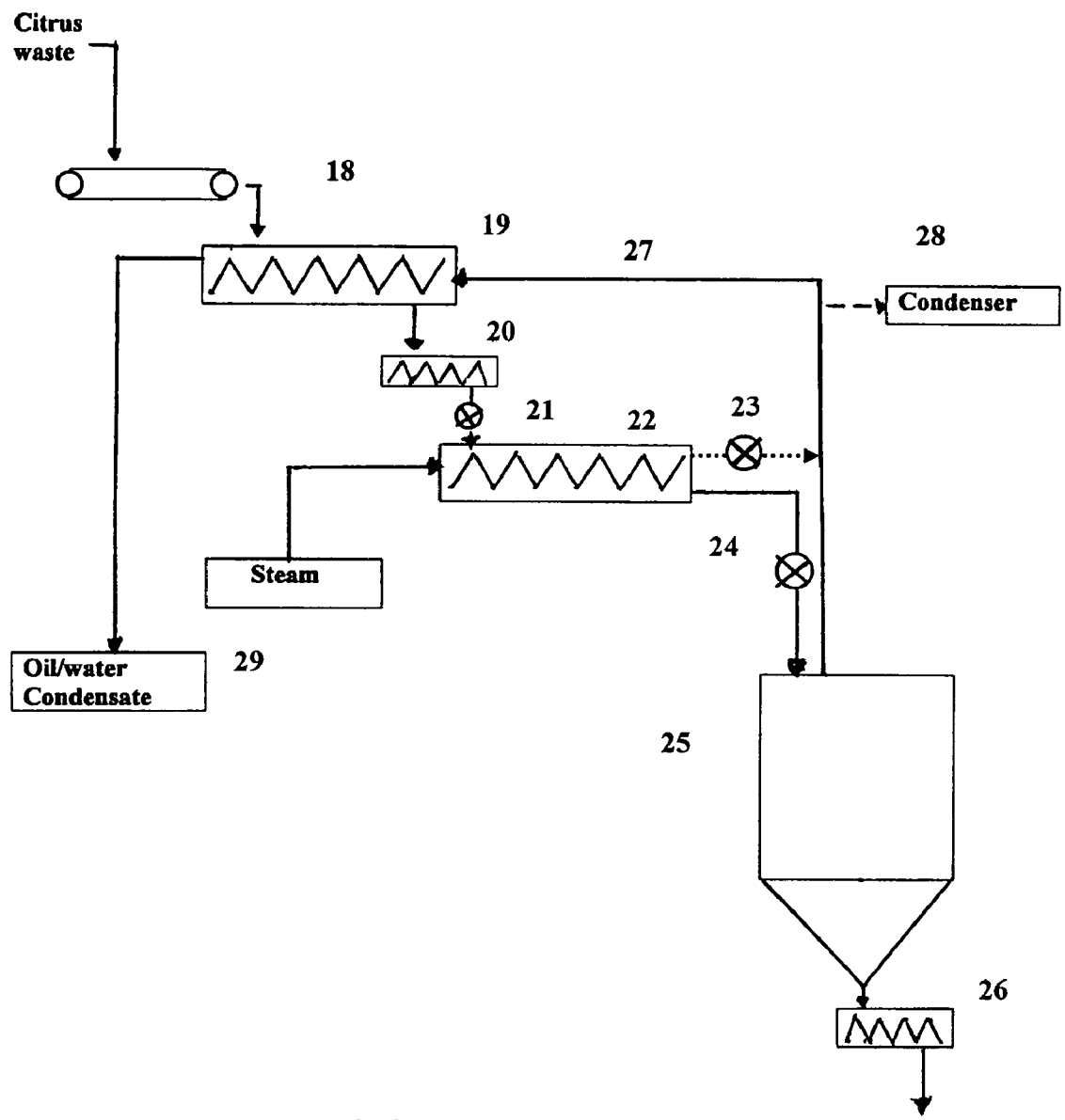
FIG. 2 shows a flow diagram of a typical process according to this invention.

With reference to the drawings, the preferred flow diagram of the process is shown in FIG. 2 where sequence of reactors is shown. The citrus waste is fed by a belt or similar conveyor 18 to preheating agitating conveyor (preheater reactor) 19 where it is preheated by jacket, hollow flights or other indirect heating surfaces utilizing steam, hot gases or preferably peel oil/water vapors (discussed below) to provide indirect heat to the agitating conveyor 19. The preheated citrus waste is fed into main reactor 22 by a high solids pump, screw feeder or similar device 20 and rotary or other check valve 21. The citrus waste is heated to final desired temperature in enclosed, jacketed agitating conveyor/main reactor 22 using direct injection of gaseous heating medium such as steam or hot gases and combined with indirect heating through jacket, hollow flights or similar heat exchanging surfaces. Injection of steam or hot gases provides additional stripping action for peel oil and more efficient direct heat exchange with peel solids. Indirect heating decreases potential dilution of waste solids with condensed steam. The pressure in reactor 22 is maintained through controlled discharge of the hot citrus waste through rotary or similar backpressure valve 24 into flash tank 25 where hot solids and oil/water vapors are separated. Pressure control may also be regulated through an optional pressure relief or similar valve 23 which can bleed part of the peel oil/water vapors to peel oil recovery line 27. Vapors are fed to jacket and other heating surfaces of pre-heater 19 via peel oil recovery line 27 where they are condensed to an oil/water condensate 29 and provide partial heat recovery in the system. The vapors can be optionally cooled and recovered in a separate condenser 28. The pretreated and pasteurized, de-oiled solids are discharged from flash tank 25 by a high solids pump or similar device 26 and fed to the rest of the system for saccharification and fermentation.

It is to be understood that the method and system is applicable to other fruits or vegetables of similar composition, as well as to other organic matter.

The addition of lime specified in U.S. Pat. No. 3,966,984 is not necessary in our method, but we do not wish to restrict ourselves from addition of beneficial chemical agents such as acids or bases, either before, during or after the heating process. In order to achieve the efficient heat transfer to the bulk of citrus waste particles, the particles need to be separated (fluffed) by agitation to allow circulation of heat transferring agents, such as saturated or unsaturated (superheated) steam or hot gases between particles. It is an added benefit if the heating and mixing device also conveys the material because the cost of additional equipment is eliminated.

Thus, in view of FIGS. 1 and 2, there is provided a system for pretreating citrus waste to remove peel oil components, pasteurize and disrupt cell structure as a pretreatment of the citrus waste solids for further enzymatic hydrolysis and microbial fermentation, comprising optional size reducing means to reduce the particle size of the citrus waste prior to preheating; conveying means to convey citrus waste into and through the system; indirect preheating means to preheat the citrus waste; indirect and direct heating means to heat the preheated citrus waste and produce pasteurized citrus waste solids with disrupted cell structure and a vapor containing water and peel oil components; separating means to separate the pasteurized citrus waste solids and vapor containing water and peel oil components to produce separated pasteurized citrus waste solids and separated vapor containing water and peel oil components; heat recovery means to convey separated vapor containing water and peel oil components to said indirect preheating means; optional cooling means to cool pasteurized citrus waste solids; and optional means to enzymatically saccharify such cooled waste and ferment it using yeasts or other microorganisms.

The size reducing means comprises means to reduce the particle size of the citrus waste prior to heating. Size reducing means are well known in the art and includes, for example, hammer mills, disc mills or other suitable grinders, choppers, shredders and mills 2.

The conveying means comprises means to convey citrus waste into and through the system. Conveying means are well known in the art and includes, for example, a belt or similar conveyor 18 to convey citrus waste to preheating agitating conveyor (preheater reactor) 19; a high solids pump, screw feeder or similar device 20 and rotary or other check valve 21 to convey preheated citrus waste to main reactor 22; rotary or similar valve 24 to convey heated citrus waste to flash tank 25; and a high solids pump or similar device 26 to convey de-oiled solids from flash tank 25 to the rest of the system for saccharification and fermentation.

Indirect preheating means comprises means to preheat the citrus waste. Indirect preheating means are well known in the art and includes, for example, preheating agitating conveyor (preheater reactor) 19 where citrus waste is preheated by jacket, hollow flights or other indirect heating surfaces; steam, hot gases or preferably peel oil/water vapors (discussed herein) provide indirect heat to the agitating conveyor 19.

Indirect and direct heating means comprise means to heat the preheated citrus waste and produce pasteurized citrus waste solids and a vapor containing water and peel oil components. Indirect and direct heating means are well known in the art and includes, for example, enclosed, jacketed agitating conveyor/main reactor 22 where the preheated citrus waste is heated using a combination of indirect heating by jacket, hollow flights or similar heat exchanging surfaces and direct injection of gaseous heating medium such as steam or hot gases.

Separating means comprises means to separate the pasteurized citrus waste solids and vapor containing water and peel oil components to produce separated pasteurized citrus waste solids with low oil content and separated vapor containing water and peel oil components. Separating means are well known in the art and includes, for example, flash tank 25 where hot solids and oil/water vapors are separated. Vapors are fed to jacket and other heating surfaces of pre-heater 19 via peel oil recovery line 27 and the de-oiled solids are discharged from flash tank 25 by a high solids pump or similar device 26 and fed to the rest of the system for optional cooling and saccharification and fermentation as outlined in FIG. 1.

Heat recovery means comprises means to convey separated vapor containing water and peel oil components to indirect preheating means. Heat recovery means are well known in the art and includes, for example, flash tank 25 where hot solids and oil/water vapors are separated and vapors are fed to jacket and other heating surfaces of pre-heater 19 via peel oil recovery line 27 where they are condensed to an oil/water condensate 29 and provide partial heat recovery in the system.

Cooling means comprises means to cool separated pasteurized citrus waste solids. Cooling means are well known in the art and includes vacuum, direct or indirect heat exchange means.

Saccharification and fermentation means comprises means to saccharify (e.g., using enzymes) and ferment (e.g., using yeasts or other microorganisms) said separated pasteurized citrus waste solids. Saccharification and fermentation means are well known in the art.

Unless defined otherwise, all technical and scientific terms used herein have the same meaning as commonly understood by one of ordinary skill in the art to which the invention belongs. Any methods and materials similar or equivalent to those described herein can be used in the practice or testing of the present invention.

All of the references cited herein are incorporated by reference in their entirety. Also incorporated by reference in their entirety are the following U.S. Pat. Nos. 1,973,084; 3,966,984; 6,183,806; 6,151,799. Also incorporated by reference in its entirety is U.S. Patent Application Publication 20060177916.

Thus, in view of the above, the present invention concerns (in part) the following:

A method of pretreating citrus waste, said method comprising (or consisting essentially of or consisting of) pretreating said citrus waste by preheating said citrus waste through indirect heating in a preheater reactor to form preheated citrus waste and conveying said preheated citrus waste to a main reactor, heating said preheated citrus waste through a combination of (simultaneous) indirect and direct heating in a main reactor to produce pasteurized citrus waste solids and a vapor containing water and peel oil components; and separating said pasteurized citrus waste solids and said vapor containing water and peel oil components to produce separated pasteurized citrus waste solids and separated vapor containing water and peel oil components; said method comprising optionally reducing the particle size of said citrus waste prior to said preheating.

The above method, further comprising cooling said separated pasteurized citrus waste solids to produce cooled pasteurized citrus waste solids.

The above method, wherein the concentration of limonene in said cooled pasteurized citrus waste solids is below about 3,000 ppm (e.g., 100-less than 3,000 ppm).

The above method, wherein the concentration of limonene in said cooled pasteurized citrus waste solids is below about 1,500 ppm (e.g., 100-less than 1,500 ppm).

The above method, further comprising saccharifying and fermenting said cooled pasteurized citrus waste solids.

The above method, wherein said preheater reactor is indirectly heated by said separated vapor containing water and peel oil components and wherein said separated vapor containing water and peel oil components is condensed to form condensed water and peel oil components. The above method, wherein said condensed water and peel oil components are separated into water and oil fractions.

The above method, wherein said method is operated on a continuous basis.

The above method, wherein the microbial count in said cooled pasteurized citrus waste solids exhibits at least a 5 log reduction in microbial colony forming units in comparison to untreated citrus waste.

A system for pretreating citrus waste, comprising (or consisting essentially of or consisting of) conveying means to convey citrus waste into and through the system, indirect preheating means to preheat the citrus waste, indirect and direct heating means to heat the preheated citrus waste and produce pasteurized citrus waste solids and a vapor containing water and peel oil components, separating means to separate the pasteurized citrus waste solids and vapor containing water and peel oil components to produce separated pasteurized citrus waste solids and separated vapor containing water and peel oil components, heat recovery means to convey separated vapor containing water and peel oil components to said indirect preheating means.

The above system, further comprising size reducing means to reduce the particle size of said citrus waste prior to said preheating.

The above system, further comprising cooling means to cool said separated pasteurized citrus waste solids.

The above system, further comprising saccharification and fermentation means to saccharify and ferment said separated pasteurized citrus waste solids.

Method of pretreatment of citrus waste for enzymatic saccharification and fermentation by yeast or other microorganisms which includes pasteurization of citrus solids, removal and recovery of peel oil components, including limonene, such method comprising (or consisting essentially of or consisting of: (a) subdividing a citrus residue having volatile citrus oil components, including limonene, and water; (b) heating, agitating and conveying such residue in one or two stages where said heating is to a final temperature sufficiently high to pasteurize and rupture citrus waste cells to facilitate subsequent hydrolysis and fermentation steps, release essential oil, including limonene and to evaporate part of oil components and portion of water to form vapor component comprising water, limonene and other volatile oil components; (c) releasing heated and ruptured citrus waste to atmospheric pressure at temperature sufficiently high to evaporate additional part of peel oil components, including limonene, and water; (d) collecting and condensing said vapor component; and (e) cooling pretreated, de-oiled citrus waste.

The above method in which citrus waste is preheated in jacketed, horizontal or vertical conveying/mixing device using indirect heat from oil/water vapors, steam or hot gases.

The above method in which oil/water vapors from main reactor and stripper are condensed in heating side of preheater reactor.

The above method in which condensed oil/water vapors are separated into water and oil fractions.

The above method in which citrus waste is heated in jacketed, enclosed horizontal or vertical conveying/mixing device equipped with injectors for steam or hot gases.

The above method in which conveying/mixing means comprise hollow or solid, continuous or interrupted flights or paddles The above method in which citrus waste is heated by a combination of direct and indirect heat exchanging means.

The above method in which said method is operated on continuous basis.

The above method in which said citrus waste includes press cake.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method of pretreating solid citrus waste, said method comprising pretreating said solid citrus waste by preheating said solid citrus waste through indirect heating in a preheater reactor to form preheated solid citrus waste and conveying said preheated solid citrus waste to a main reactor, heating said preheated solid citrus waste at a temperature of about 90° to about 200° C. through a combination of indirect and direct heating in a main reactor to produce pasteurized citrus waste solids and a vapor containing water and peel oil components, separating said pasteurized citrus waste solids and said vapor containing water and peel oil components to produce separated pasteurized citrus waste solids and separated vapor containing water and peel oil components, cooling said separated pasteurized citrus waste solids to produce cooled pasteurized citrus waste solids, and saccharifying and fermenting said cooled pasteurized citrus waste solids; said method comprising optionally reducing the particle size of said citrus waste prior to said preheating.

2. The method according to claim 1, wherein the concentration of limonene in said cooled citrus waste solids is below about 3,000 ppm.

3. The method according to claim 1, wherein the concentration of limonene in said cooled pasteurized citrus waste solids is below about 1,500 ppm.

4. The method according to claim 1, wherein said preheater reactor is indirectly heated by said separated vapor containing water and peel oil components and wherein said separated vapor containing water and peel oil components is condensed to form condensed water and peel oil components.

5. The method according to claim 4, wherein said condensed water and peel oil components are separated into water and oil fractions.

6. The method according to claim 1, wherein said method is operated on a continuous basis.

7. The method according to claim 2, wherein the microbial count in said cooled pasteurized citrus waste solids exhibits at least a 5 log reduction in microbial colony forming units in comparison to untreated citrus waste.

8. The method according to claim 1, wherein said preheating is conducted at a temperature of about 55° to about 99° C.

9. The method according to claim 1, wherein said heating is conducted at a temperature of about 100° to about 160° C.

10. The method according to claim 1, wherein said heating is conducted at a pressure of 0 to 300 psi.

11. The method according to claim 1, wherein said heating is conducted for about 1 to about 300 minutes.

12. The method according to claim 1, wherein said method consists essentially of pretreating said solid citrus waste by preheating said solid citrus waste through indirect heating in a preheater reactor to form preheated solid citrus waste and conveying said preheated solid citrus waste to a main reactor, heating said preheated solid citrus waste at a temperature of about 90° to about 200° C. through a combination of indirect and direct heating in a main reactor to produce pasteurized citrus waste solids and a vapor containing water and peel oil components, separating said pasteurized citrus waste solids and said vapor containing water and peel oil components to produce separated pasteurized citrus waste solids and separated vapor containing water and peel oil components, cooling said separated pasteurized citrus waste solids to produce cooled pasteurized citrus waste solids, and saccharifying and fermenting said cooled pasteurized citrus waste solids; said method comprising optionally reducing the particle size of said citrus waste prior to said preheating.

13. The method according to claim 1, wherein said method consisting of pretreating said solid citrus waste by preheating said solid citrus waste through indirect heating in a preheater reactor to form preheated solid citrus waste and conveying said preheated solid citrus waste to a main reactor, heating said preheated solid citrus waste at a temperature of about 90° to about 200° C. through a combination of indirect and direct heating in a main reactor to produce pasteurized citrus waste solids and a vapor containing water and peel oil components, separating said pasteurized citrus waste solids and said vapor containing water and peel oil components to produce separated pasteurized citrus waste solids and separated vapor containing water and peel oil components, cooling said separated pasteurized citrus waste solids to produce cooled pasteurized citrus waste solids, and saccharifying and fermenting said cooled pasteurized citrus waste solids; said method comprising optionally reducing the particle size of said citrus waste prior to said preheating.

14. The method according to claim 1, wherein water is added in said method only in the form of steam during said heating.

* * * * *